(12) United States Patent
Kahlon (10) Patent No.: US 11,510,798 B1
(45) Date of Patent: Nov. 29, 2022

(54) INTRAVASCULAR ULTRASOUND (IVUS) OSTIAL STENT DELIVERY SYSTEM AND METHOD

(71) Applicant: Arunpreet Kahlon, Cheyenne, WY (US)

(72) Inventor: Arunpreet Kahlon, Cheyenne, WY (US)

(73) Assignee: Arunpreet Kahlon, Highlands Ranch, CO (US)

( * ) Notice: Subject to any disclaimer, the term of this patent is extended or adjusted under 35 U.S.C. 154(b) by 0 days.

(21) Appl. No.: 17/472,450

(22) Filed: Sep. 10, 2021

(51) Int. Cl.
*A61F 2/958* (2013.01)
*A61B 8/12* (2006.01)
*A61B 8/00* (2006.01)

(52) U.S. Cl.
CPC ............... *A61F 2/958* (2013.01); *A61B 8/12* (2013.01); *A61B 8/4254* (2013.01); *A61B 8/4422* (2013.01); *A61B 8/4461* (2013.01); *A61B 8/4488* (2013.01)

(58) Field of Classification Search
CPC ......... A61F 2/958; A61B 8/12; A61B 8/4254; A61B 8/4422; A61B 8/4461; A61B 8/4488
See application file for complete search history.

(56) References Cited

U.S. PATENT DOCUMENTS

| 6,780,199 B2 | 8/2004 | Solar et al. |
| 7,651,521 B2 | 1/2010 | Ton et al. |
| 2009/0182281 A1* | 7/2009 | Kurth .................. A61M 25/0113 604/164.08 |
| 2012/0108979 A1* | 5/2012 | Franklin ................ A61B 8/445 600/463 |

(Continued)

FOREIGN PATENT DOCUMENTS

| WO | WO-9934749 A1 | 7/1999 | |
| WO | WO-2021058286 A1 * | 4/2021 | ............... A61B 8/12 |

OTHER PUBLICATIONS

Lichaa, Hady, et al., "Coronary stent positioning under live IVUS guidance in low contrast percutaneous coronary interventions: The live IVUS stenting technique", Wiley, Catheter Cardiovasc Interv. 2021;1-8., (2021), 9 pgs.

*Primary Examiner* — Serkan Akar
*Assistant Examiner* — Amal Aly Farag
(74) *Attorney, Agent, or Firm* — Schwegman Lundberg & Woessner, P.A.

(57) ABSTRACT

For deploying a stent at a coronary ostium, an integrated intravascular ultrasound (IVUS) ostial stent delivery apparatus can include a balloon catheter and an elongate shaft defining (1) a longitudinal inflation lumen and (2) a longitudinal IVUS lumen. A balloon can be located at and about the distal shaft portion and inflated with the inflation lumen. The shaft further defines a longitudinal guidewire lumen, extending at least through the distal shaft portion underlaying the balloon for at least a length of the balloon along the shaft. The IVUS lumen can include removable IVUS ultrasound imaging transducer with a signal conduit to external processing and display componentry. The imaging can help ensure proper stent location before placement and deployment, or for post-placement and stent deployment confirmation, without requiring removal of the stent delivery device to deploy a separate IVUS imaging probe.

23 Claims, 9 Drawing Sheets

(56) References Cited

U.S. PATENT DOCUMENTS

| | | | |
|---|---|---|---|
| 2013/0023802 A1* | 1/2013 | McIntosh | A61M 25/10 601/2 |
| 2014/0128726 A1 | 5/2014 | Quill et al. | |
| 2014/0276028 A1* | 9/2014 | Stigall | A61M 25/0108 600/463 |
| 2015/0265816 A1* | 9/2015 | Campbell | A61M 25/104 606/194 |
| 2020/0360164 A1 | 11/2020 | Janku et al. | |
| 2021/0259860 A1* | 8/2021 | Walzman | A61F 2/852 |

* cited by examiner

Fig. 4

INTRAVASCULAR ULTRASOUND (IVUS) OSTIAL STENT DELIVERY SYSTEM AND METHOD

TECHNICAL FIELD

This document relates generally to vascular intervention, interventional cardiology, radiology, vascular surgery, and particularly, but not by way of limitation to an intravascular ultrasound (IVUS) ostial stent delivery system and method.

BACKGROUND

A stent is a type of an endoprosthesis device. A stent may be placed or implanted within a vein, artery, or other tubular body organ or vessel, such as for treating occlusions, stenoses, or aneurysms of a vessel by reinforcing the wall of the vessel or by expanding the vessel. A stein is generally a longitudinal tubular device of biocompatible material, for example, stainless steel, cobalt-chromium, nitinol, or a biodegradable material, providing a flexible scaffold framework of struts that can be radially expanded, such as by using a balloon catheter, or self-expanded within the vessel, such as by using a shape memory characteristic of the material. The struts are configured to move and thereby to allow the stent to be compressed or "crimped" into a smaller outer diameter so that they can be mounted inside a stem delivery system such as for delivery to, and expandable deployment at, a desired intravascular location.

While only a relatively small percentage of stents are deployed at an ostium, ostial stenting is a particularly important and challenging location for deploying a stent. An ostium refers to the mouth of the blood vessel, at which it joins another vascular structure. For example, a coronary artery can exit the aorta just above the aortic valve at a coronary ostium. Similarly, a renal artery may exit the aorta at an ostium. While attempting to deploy a stent accurately at an ostium of a vessel, it may be very difficult to position the stent at the true ostium of the vessel. For example, stenting a lesion located at such a coronary ostium involves properly placing and deploying the stent in a manner that spans the coronary ostium not too deep into the coronary vessel such that the ostium is not supported by the expanded stent but also in a manner such that the stent does not protrude from the coronary ostium out into the aorta. A protruding stent can cause blood flow turbulence, and can impede any later intervascular stenting procedure, such as at a location along the aorta that is located beyond any such protruding stent.

Proper stent placement at an ostium is difficult to verify fluoroscopically or angiographically. For example, directionality of such ostial structures is difficult to ascertain from an angiographic 2-dimensional (2D) projection of a 3-dimensional (3D) blood vessel structure. In 3D, the blood vessel structure can exhibit bends and turns in all 3 dimensions. Depending on the angle from which the X-ray fluoroscopy image is 2.0 obtained, the blood vessel can appear shortened. Any misrepresentation of the ostium on the X-ray projection used in fluoroscopic imaging can therefore lead to the possibility of mispositioning the stent with respect to the desired ostium location.

Intravascular Ultrasound (IVUS) imaging can be used for imaging atherosclerosis and other vessel diseases and defects. In an IVUS imaging procedure, an IVUS catheter is threaded over a guidewire into a blood vessel of interest. IVUS images are acquired of the atherosclerotic plaque and surrounding area. Existing IVUS imaging techniques, however, generally involve removing the IVUS imaging catheter from the guidewire, then inserting a stent delivery apparatus over the guidewire to deliver and deploy the stent at a desired location. After stent delivery and deployment, the stent delivery apparatus is removed. Then, the IVUS imaging catheter is re inserted for further imaging to confirm proper stent deployment.

SUMMARY

The present inventor has recognized, among other things, that existing IV US techniques are time-consuming and inconvenient. In particular, existing IVUS techniques are not well-suited for the less common but particularly challenging task of placing and deploying an ostial stent. Even if the interventional cardiologist were to exchange the stent delivery apparatus for an IVUS imaging catheter, to confirm proper stent placement and deployment, the present inventor has recognized that it would be far more advantageous to have a convenient and usable system for employing IVUS to determine proper stent location before deploying the stent, so that the stent can actually be properly deployed at the desired location with respect to the ostium.

One approach to using intravascular imaging for assisting in stent placement and employment might be to insert into a guide catheter: (1) a separate IVUS imaging catheter (e.g., over a first guidewire) and (2) a separate balloon catheter stent delivery device (e.g., over a second guidewire). However, an approach using a separate IVUS imaging catheter and a separate stent delivery device is bulky and may be unusable in a stenosed blood vessel or ostium to be treated.

For example, the present document describes an integrated (unitary) intravascular ultrasound (IVUS) imaging transducer that can be carried onboard and combined with an ostial stent delivery apparatus, such as which can be used in a method of deploying a stent at a blood vessel ostium. First, a balloon carrying a stent can be inserted into a coronary blood vessel ostium using a balloon catheter of the stent delivery apparatus. Second, the ostium can be intravascularly imaged, such as from an imaging transducer that is located with the stent delivery apparatus, such as at a location that is at least in part proximal to the balloon carrying the stein. This imaging can be used to determine a stent location with respect to the ostium. Third, when the imaging indicates that the stent is at the desired stent location with respect to the ostium, then the balloon can be expanded to expandably deploy the stent at the desired stent location.

This method can include inserting an intravascular ultrasound (IVUS) s transducer as part of an integrated unitary stent delivery apparatus that also includes the balloon, sharing a common elongate shaft, such that both the IVUS transducer and the balloon can be introduced into the vasculature, via a guidewire, as a single unitary instrument. For example, the transducer can be inserted in a fixed arrangement with respect to the balloon.

Alternatively (or additionally), this method can include inserting a removable intravascular ultrasound (IVUS) transducer to a desired location with respect to the balloon via an IVUS lumen that is in a fixed arrangement with respect to the balloon. Optionally, the method can further include removing the ultrasound transducer by extracting the ultrasound transducer via the IVUS lumen to an external location. Optionally, the removable ultrasound transducer can be at least one of reprocessed or resterilized, such as for allowing re-use of ultrasound transducer for a subsequent procedure.

Optionally, the method can further include: deflating the balloon; further inserting (or alternatively slightly retracting) the balloon catheter of the stent delivery apparatus; and further imaging via the transducer to confirm stent deployment and desired apposition with respect to the vascular structure of the blood vessel, the ostium, or both.

The method can include inserting a portion of the balloon catheter using one or both of a monorail/rapid-exchange or an over-the-wire technique.

In an example, the integrated intravascular ultrasound (IVUS) ostial stent delivery apparatus can include a balloon catheter. The balloon catheter can include an elongate shaft having a proximal shaft portion and a distal shaft portion and defining (1) a longitudinal inflation lumen and (2) a longitudinal IVUS lumen extending between the proximal shaft portion and the distal shaft portion. A balloon can be located at and about the distal shaft portion and in fluid communication with the inflation lumen. The shaft further defines a longitudinal guidewire lumen, extending at least through the distal shaft portion underlaying the balloon for at least a length of the balloon along the shaft. An IVUS ultrasound imaging transducer is at least one of locatable at or affixed to the distal shaft portion and located at least in part proximally to the balloon to permit imaging of a coronary blood vessel ostium including before expandably deploying a stent at or near the ostium by inflating the balloon. The balloon catheter can also include a transduced IVUS signal conduit coupled to the transducer and passing through the IVUS lumen to the proximal shaft portion for coupling to and signal processing by patient-external processing circuitry couplable thereto.

In an example, the integrated intravascular ultrasound (IVUS) ostial stent delivery apparatus can include a balloon catheter. The balloon catheter can include an elongate shaft having a proximal shaft portion and a distal shaft portion and defining (1) a longitudinal inflation lumen and (2) a longitudinal IVUS lumen extending between the proximal shaft portion and the distal shaft portion. A balloon can be located at and about the distal shaft portion and in fluid communication with the inflation lumen. The shaft further defines a longitudinal guidewire lumen, extending at least through the distal shaft portion underlaying the balloon for at least a length of the balloon along the shaft. The IVUS lumen is sized and shaped and arranged to pass an IVUS ultrasound imaging transducer to a location at or just proximal to the balloon to permit imaging of a coronary blood vessel ostium including before expandably deploying a stent at or near the ostium by inflating the balloon.

The present document describes techniques that can allow real-time image-guidance any of before, during, and after stent delivery and deployment, such as can be particularly useful in the challenging case of properly placing and deploying a stent at a coronary ostium. This can help avoid problems with sub-optimal ostial stent placement or deployment, such as explained herein.

BRIEF DESCRIPTION OF THE DRAWINGS

In the drawings, which are not necessarily drawn to scale, like numerals may describe similar components in different views, Like numerals having different letter suffixes may represent different instances of similar components. The drawings illustrate generally, by way of example, but not by way of limitation, various embodiments discussed in the present document.

DETAILED DESCRIPTION

The present techniques can be useful for IVUS image-guided stent placement at a blood vessel ostium (e.g., coronary vessel ostium, renal vessel ostium, or the like) to treat an ostial lesion. An IVUS transducer can be integrated with the stent delivery device. This can give the physician better visualization information. Such IVUS imaging information can include accurate 3-dimensional (3D) full circumferential (e.g., 360 degrees) visualization information. The IVUS imaging information can be used by the physician in real-time, such as to help avoid placing the stent sub-optimally. An example of sub-optimal ostial stent placement includes placing the stent too deep within a blood vessel lumen so as to be ineffective at treating the ostial lesion. Another example of sub-optimal ostial stent placement includes placing the stent protruding too-far out of the blood vessel ostium into source vasculature. Such a protruding stent can create blood flow turbulence and can impede subsequent stenting procedures. The present techniques can help provide better imaging information to the physician for guiding stent placement than what is available using fluoroscopy or angiography.

Figure 1A:
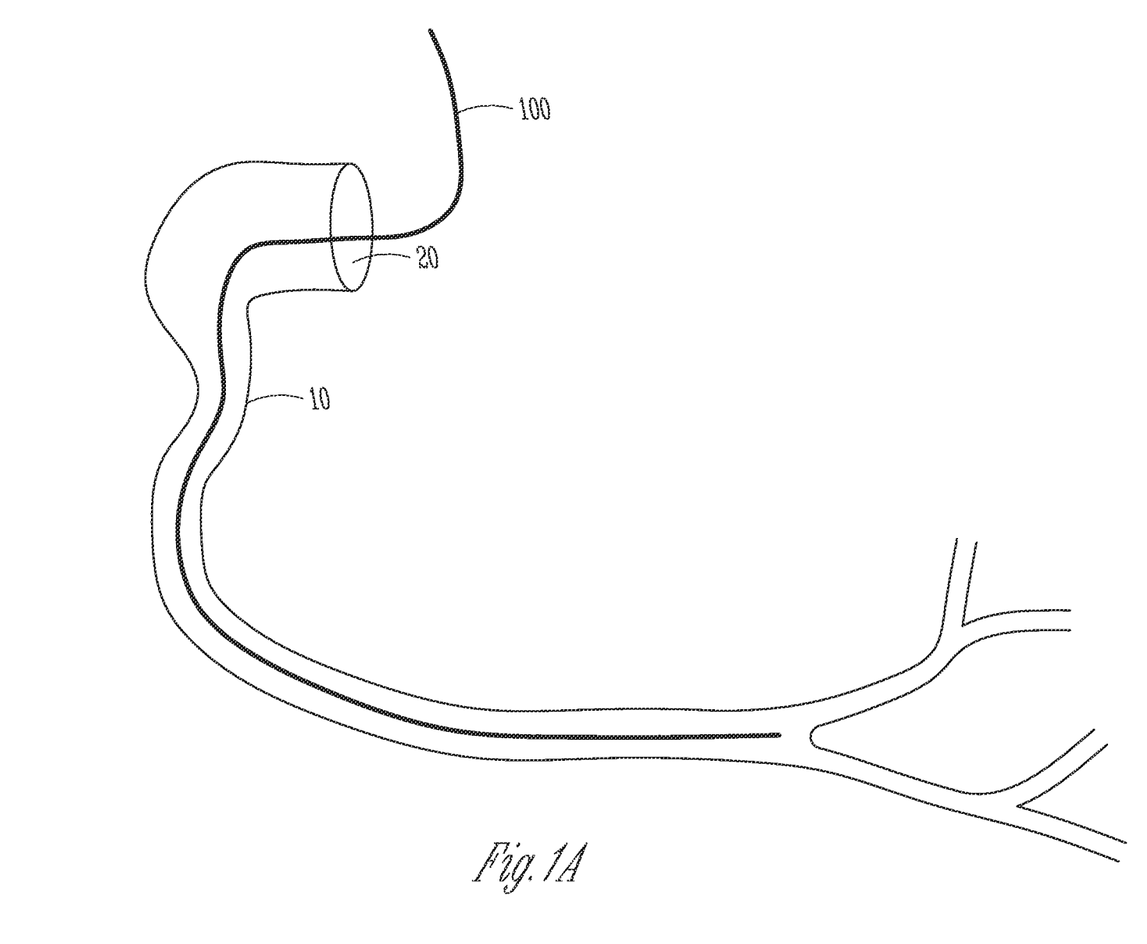
FIG. 1A is a schematic illustration of a coronary vessel with a guidewire having been introduced into the coronary vessel through the coronary ostium.

FIG. 1A is a schematic illustration of a blood vessel, such as a coronary artery 10. A guidewire 100 has been introduced, via a guide catheter (not shown), into the coronary vessel 10, through the coronary ostium 20. The ostium 20 opens into a larger vascular structure, such as the aorta. For treating an ostial lesion via a stent, it is desired to place the stent such that a proximal end of the stent either (1) aligns with the plane defined by the ostium 10 opening into the larger vascular structure of the aorta, or (2) such that the proximal end of the stent only minimally protrudes into such larger vascular structure of the aorta.

Figure 1B:
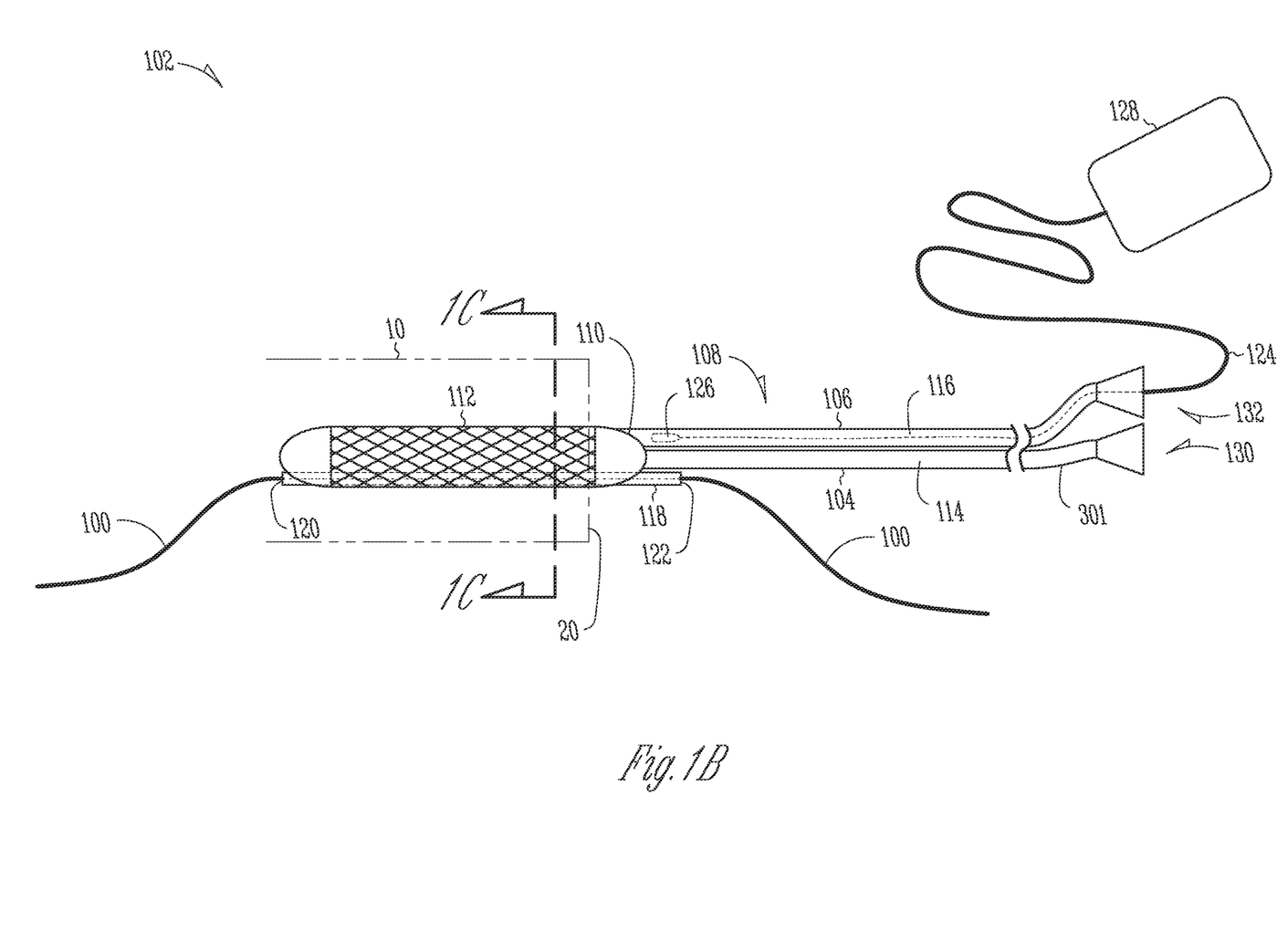
FIG. 1B is a schematic illustration showing a side view of portions of an embodiment of a guided stent delivery system that can include a stent delivery device.

FIG. 1B is a schematic illustration showing a side view of portions of an embodiment of an image-guided stent delivery system that can include a stent delivery device 102. In FIG. 1B, the stent delivery device 102 is shown with the guidewire 100 extending through the coronary vessel 10 and its ostium 20. In FIG. 1B, the stent delivery device 102 includes an integrated stent-delivery balloon catheter and IVUS catheter sharing a common elongate shaft 108. A distal portion of the elongate shaft 108 includes a balloon 110 about an outer circumference of the elongate shaft 108. The uninflated balloon 110 carries an unexpanded stent 112. In FIG. 1B, the stent 112 is shown, with respect to the ostium 20, with the proximal end of the stent 112 being aligned with the plane defined by the ostium 20 opening into the larger vascular structure of the aorta, such as is desired for good ostial stenting.

The shaft 108 can include a first hypotube or other similar tubular inflation tube 104 structure defining an inflation lumen 114. The inflation lumen 114 is arranged to provide a fluid communication conduit extending from within the balloon 110, located at the distal portion of the shaft 108, to a proximal portion of the elongate shaft 108. At or near the proximal end of the elongate shaft 108, the fluid communication conduit of the inflation lumen 114 can include a Luer coupling. The Luer coupling can provide a port for providing a further fluid communication conduit passage for coupling to a syringe or pump or other fluid inflation and deflation source that is located external to the patient. The balloon 110 can be inflated by pumping or otherwise directing a quantity of an inflation fluid (e.g., saline solution and fluoroscopic imaging contrast agent mixture) from the inflation and deflation source. The fluid is directed toward the balloon 110 via the inflation lumen 114, such as for inflating the balloon 110. Inflating the balloon 110 expands the stent 112. Expanding the stent 112 deploys the stent 112 into apposition with the vasculature, such as with a proximal end of the stent 112 aligned with the plane defined by the opening of the ostium 20 into the larger vascular structure of the aorta. The syringe or other inflation or deflation source can be used to withdraw fluid from the balloon 110 via the inflation lumen 114 to deflate the balloon 110, leaving the expanded stent 112 deployed and supporting the surrounding vascular region.

The shared elongate shaft 108 can also include a second hypotube or other similar tubular IVUS tube 106 structure defining an IVUS lumen 116. For example, the IVUS lumen 116 can extend from a proximal portion of the shaft 108 at least to a proximal edge of they balloon 110. The IVUS lumen 116 may terminate at the proximal edge of the balloon 110. Alternatively, the IVUS lumen 116 may optionally extend even further into a distal portion of the shaft 108 underlying the balloon 110. The IVUS lumen 116 can extend distally beyond the distal edge of the balloon 110, such as toward the distal tip of the elongate shaft 108. The IVUS lumen 116 can be hermetically sealed, including at its termination location at the distal portion of the elongate shaft 108 of balloon catheter 114, such as to inhibit fluid ingress into the IVUS lumen 116 from within the vasculature.

The IVUS lumen 116 can be sized, shaped, and otherwise configured to allow passage or carrying of an elongate IVUS probe 124 or catheter, such as can be either fixed within or removably inserted within the IVUS lumen 116. For example, the IVUS tube 106 can define an IVUS lumen 116 having an inner diameter of 1 mm or less. The IVUS probe 124 includes an IVUS transducer 126, such as can be located at a distal portion or distal tip of time IVUS probe. For example, the IVUS transducer 126 can include either a spinnable component to provide 360 degree circumferential imaging from various different circumferential locations, or a phase-array or scannable set of components to provide 360 degree circumferential imaging from various different circumferential locations. The IVUS transducer 126 can be located at or near a distal portion of the IVUS probe 124. For example, all or a portion of the IVUS transducer 126 can be located just proximal to the balloon 110. Alternatively, all or a portion of the IVUS transducer 126 can optionally be located or locatable under all or a portion of the balloon 110 extending about the elongate shaft 108.

The IVUS probe 124 provides an IVUS signal communication conduit for the transduced IVUS signal, back from the IVUS transducer 126 through the IVUS probe 124 and to external interface componentry 128 coupled thereto. Time external interface componentry can include a pullback actuator or motor and instrumentation circuitry, which can include a microprocessor or other signal processing circuitry, such as for signal-processing the IVUS transducer signal data into a 360 degree circumferential visualization image. The pullback actuator or motor can be used to withdraw the IVUS transducer 126 at a specified rate, while concurrently taking 360 degree circumferential images that can be stitched together to form a cylindrical 360 degree image over the longitudinal distance traversed by the IVUS transducer 126 during the mechanized withdrawal. This resulting image can be displayed on a display screen for the user, such as in real-time during stent delivery and after the stent has been delivered and deployed.

As explained further below, because the IVUS transducer 126 is located at a specified distance from an edge of the stent 112 on the stent delivery device 102, the stent delivery device 102 can be inserted into the coronary vessel 10 slightly beyond the desired ostial location of the stem 112, and the pullback actuator or motor can be used to withdraw the IVUS probe to generate the cylindrical sequence of circumferential images from the IVUS transducer 126, which imaging can show the ostial plane opening into the larger vasculature of the aorta. Then, the stent delivery device 102 can similarly be withdrawn by a similar amount (with an additional incremental amount to account for a distance between the proximal edge of the stent 112 and the IVUS transducer 126). Then the balloon 110 can be expanded to properly deploy the stem 112 at the desired location with the proximal edge of the stent 112 aligned with the plane of the ostium opening into the aorta.

The shaft 108 can also include third hypotube or other similar channel structure defining a guidewire lumen 118. The guidewire lumen 118 can extend along at least along the distal portion of the shaft 108, underlying the circumferentially surrounding balloon 110. The guidewire lumen 118 can extend from a guidewire distal exit port 120, which is distal to the balloon 110, to a guidewire proximal exit port 122. The guidewire proximal exit port 122 can be located somewhat proximal to the proximal edge of the balloon 110, such as at or near the midpoint of the stent delivery device 102. As an illustrative example, the proximal exit port 122 can be 25-30 centimeters from the distal tip of the stent delivery device 102), in a "rapid-exchange" embodiment. Thus, the proximal exit port 122 can be located somewhat proximal to a proximal edge of the balloon 110 (e.g., mid-shaft, in "rapid exchange" configuration), or can be located anywhere more proximally even at or near the proximal end of the shaft 118 (in an "Over The Wire" or "OTW" configuration), such as illustrated in FIG. 1D.

The guidewire lumen 118 can be sized, shaped, and otherwise configured to pass the guidewire 100 through the guidewire lumen 118. But with the guidewire 100 already in place within a guide catheter within the vasculature, such as extending to or passing by the lesion location of interest, such as the ostium (20), the balloon catheter 104 can be introduced and passed along the guidewire (100). In this manner, the guidewire (100) can be used for introducing balloon catheter 104 to an appropriate location within the vasculature, such as for delivering, positioning, and deploying the unexpanded stent 112 such as under guidance of the visualization provided by the IVUS transducer 126 to the user. Optionally, in an OTW embodiment, the guidewire lumen 118 can extend substantially or completely along the entire length of the shaft 108 of the balloon catheter 104 to a proximal exit port 122 that is located at or near the proximal end of the shaft 108 of the balloon catheter 104.

In FIG. 1B, to recap and further explain, the stent delivery device 102 is shown as providing a balloon catheter and having an elongate shaft 108 with suitable flexibility and rigidity to be introduced intravascularly, such as via a guide catheter (see FIG. 3) and the guide wire 100, to position the distal balloon 110 carrying the stent 112 into a coronary ostium 20 and within the coronary vessel branching and extending inward therefrom. The elongate shaft 108 can include an elongate member or structure such as can include adjacent hypotubes (e.g., the inflation tube 104 and the IVUS tube 108) that can be affixed to each other, or co-formed together. These adjacent hypotubes can extend side-by-side longitudinally along the length of the elongate shaft 108, such as to respectively provide corresponding side-by-side longitudinal lumens: (1) the inflation lumen 114; and (2) the IVUS lumen 116. This arrangement of a side-by-side inflation lumen 114 and IVUS lumen 116 can extend from a proximal portion of the elongate shaft 108 to the distal portion of the elongate shaft 108, such as up to or beyond the proximal end of the balloon 110. A portion of the elongate shaft 109 can include an additional guidewire lumen 118. The guidewire lumen 118 can extend at least under the balloon 110, such as between a distal guidewire lumen port 120 and a proximal guidewire lumen port 122. The proximal guidewire lumen port 122 can be located somewhat proximal to the balloon 110, such as in a mid-portion of the elongate shaft 108, in a rapid-exchange configuration. Alternatively, the guidewire lumen 118 can extend at least under the balloon 110, such as between a distal guidewire lumen port 120 and a proximal guidewire lumen port 122 that can be located all the way at a proximal end of the elongate shaft 108, in an OTW configuration.

In an illustrative example of such an elongate shaft 108 including a side-by-side affixed pair of hypotubes, an outer diameter of the elongate shaft 108 can be approximately 2 millimeters. For example, the outer diameter of the IVUS hypotube 106 can be approximately 1 millimeter, and the outer diameter of the adjacent inflation hypotube 104 can be approximately 1 millimeter.

The inflation hypotube 104 and the IVUS hypotube 106 can individually or collectively be made of a metallic material, a non-metallic material, or a combination of these. The materials used for the inflation hypotube 104 and the IVUS hypotube 106 can be different at different locations along the length of the elongate shaft, such as to help provide a desired rigidity characteristic, a desired flexibility characteristic, or a desired ultrasound transmission characteristic at a particular location of the elongate shaft 108 or to provide a desired overall characteristic of the intravascular stent delivery device 102.

For example, the balloon inflation hypotube 104 can be made a non-metallic polymer material, such as over its most distal 40 millimeters of length along the elongate shaft 108. The inflation hypotube 104 can be made of a metal or metallic material, such as over a portion of its length that is more proximal than the distal 40 millimeters. This combination can help to improve pushability in the more proximal portion of the elongate shaft and to improve flexibility in the more distal portion of the elongate shaft. The IVUS hypotube 106 can include a non-metallic polymer material along the entire length of the elongate shaft 108, or at least in one or more regions located at or near the balloon 110 at which IVUS imaging is to be performed. 2.0 using the IV US transducer 126. This can help to transmit ultrasound through the IVUS hypotube 106 to and from the IVUS transducer 126 carried by and housed within the IVUS hypotube.

In an example, the IVUS transducer 126 can be adhesively or otherwise fixed within and to the IVUS hypotube 106, such as at a distal portion of the elongate shaft 108 at or near a proximal end of the balloon 110. Alternatively, the IVUS transducer 126 can be removable from within the IVUS hypotube 106, such as by being part of a removable IVUS probe 124 extending through—and removable from—the IVUS lumen 116. In a removable IVUS probe 124 configuration, the IVUS probe 124 can be re-usable. Such re-usability may involve re-sterilization of the removable IVUS probe 124, A re-usable IVUS probe 124 configuration may offer cost-savings over multiple procedures, such as may be performed upon different patients.

In an illustrative embodiment of a monorail/rapid exchange configuration of the stent delivery device 102, the guidewire delivery lumen 118 can extend from (1) a distal guidewire port 120 at the distal tip of the stent delivery device 102 to (2) a proximal guidewire port 122 that provides a guidewire exit located at a mid-shaft portion of the stent delivery device 102, such as at about 25-30 centimeters proximal from the distal tip of the device 102. An illustrative approximate length of the stent delivery device 102 can be in the range from 130 centimeters to 150 centimeters, and the approximate outer diameter of the stent delivery device 102 is 4 French or less. An approximate length of the stent 112 is in the range from 4 millimeters to 31 millimeters. The approximate unexpanded stent profile (outer diameter) is in the range from 1 millimeter to 1.5 millimeters. The approximate distal tip profile of the device 102 is about 0.5 millimeters.

Figure 1C:
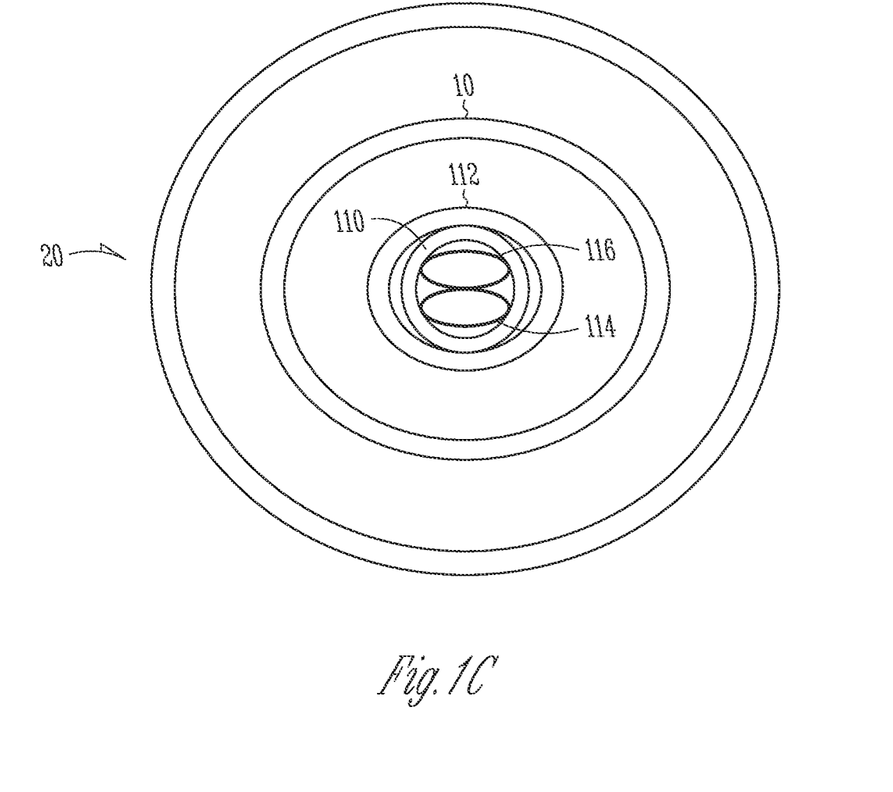
FIG. 1C shows a schematic illustration of a cross-sectional view taken along the cutline 1C-1C in FIG. 1B.
Figure 1D:
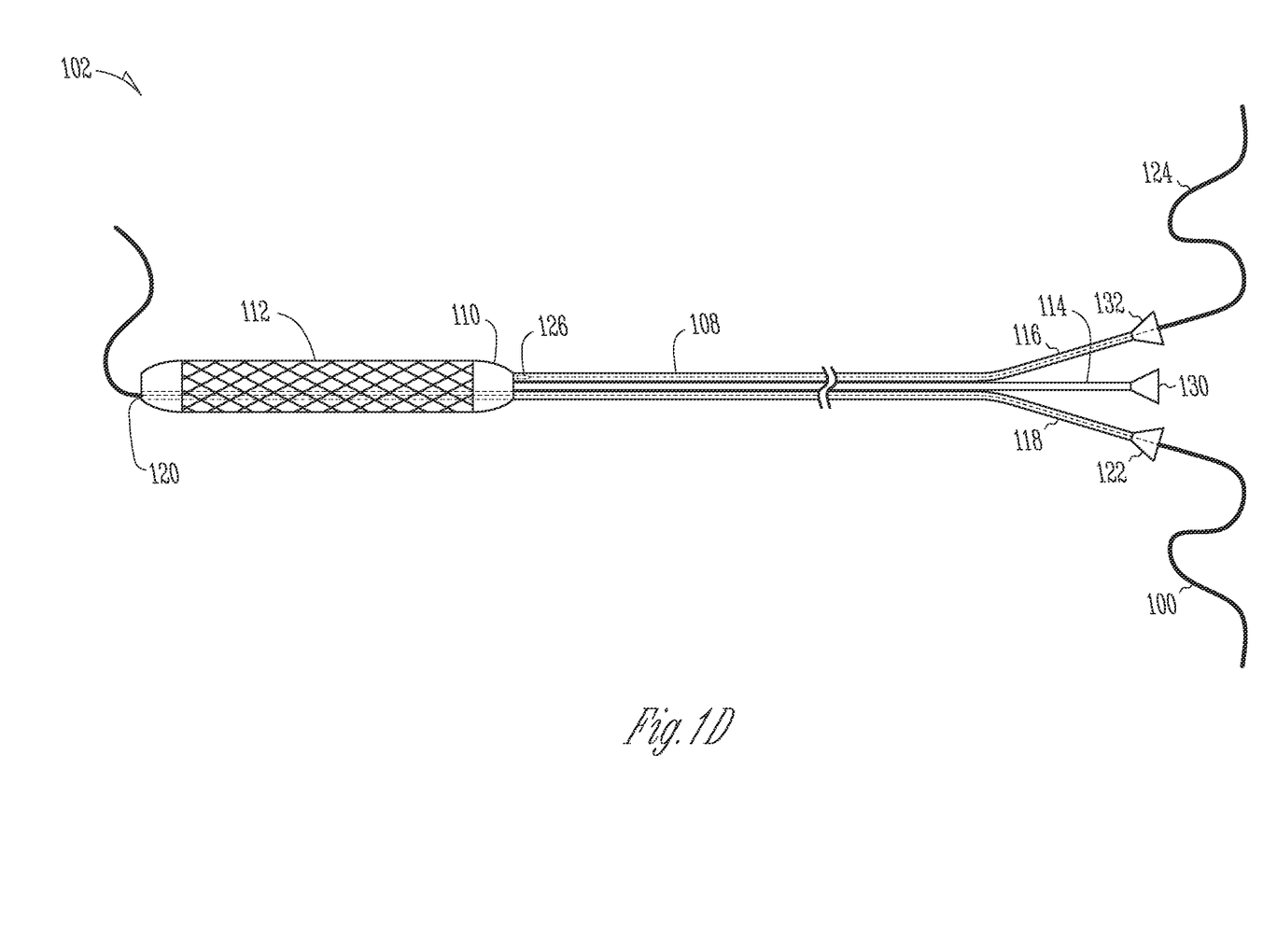
FIG. 1D is a schematic illustration showing a side view of portions of an embodiment of a guided stent delivery system that can include a stent delivery device, similar to that illustrated in FIG. 1B, but with FIG. 1D showing an Over-The-Wire (OTW) configuration in which a proximal guidewire exit port is located at a proximal end of the stent delivery device.

FIG. 1C shows a schematic illustration of a cross-sectional view taken along the cutline 1C-1C in FIG. 1B. FIG. 1C depicts a cross section of the coronary artery 10. The section of the stent delivery device 102 is represented in FIG. 1C by showing the section of the inflation hypotube 104 providing the inflation lumen 114, the section of the IVUS hypotube 106 providing the IVUS lumen 116, and the section of the unexpanded stent 112 being carried upon the section of the balloon 110.

Figure 2A:
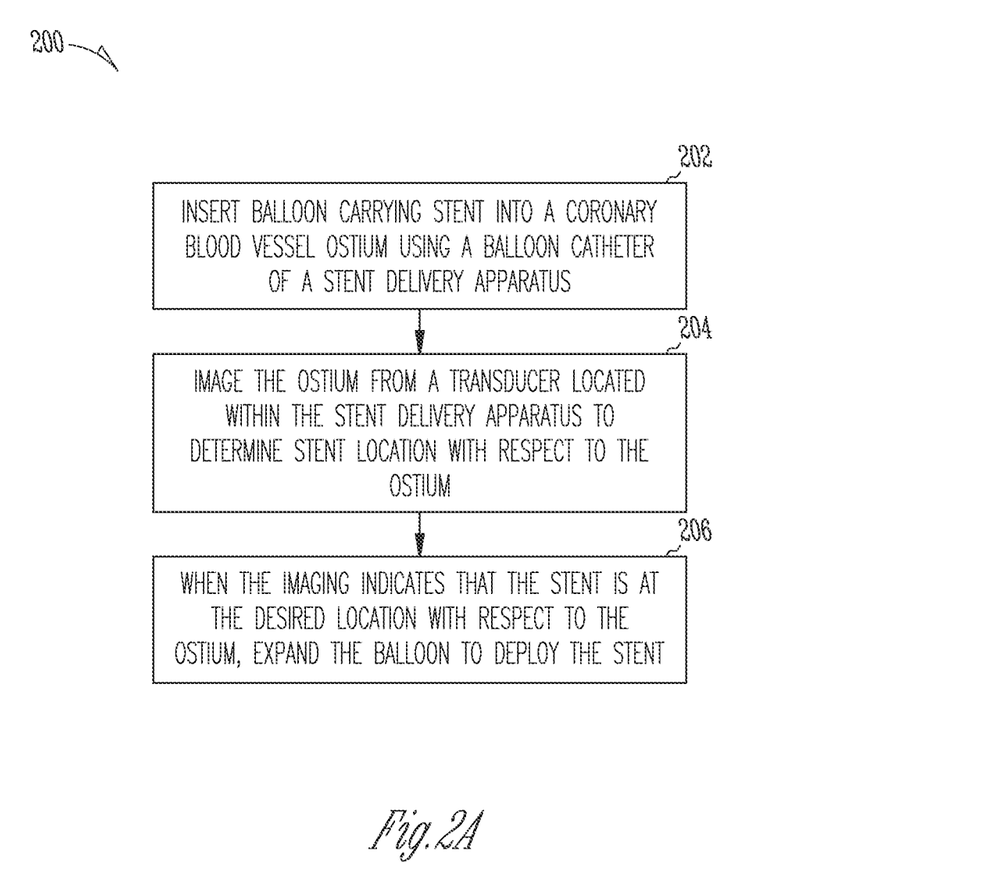
FIG. 2A is a flow chart showing an example of portions of a method of using onboard imaging of a stent delivery device to determine proper placement of a stent, before expanding and deploying the stent at the desired location using a balloon of a balloon catheter provided by the stent delivery device.

FIG. 2A is a flow chart showing an example of portions of a method 200 of using onboard imaging of a stent delivery device 102 to determine proper placement of a stent 112—including before expanding and deploying the stent 112 at the desired ostium location using a balloon 110 of a balloon catheter provided by the stent delivery device 102. Although this portion of the description may focus on a specific example of stenting a coronary blood vessel ostium, a similar approach can be taken to stent an ostium elsewhere in the vasculature, such as a renal artery ostium, a mesenteric artery ostium, or the like.

Before performing the acts shown in FIG. 2A, some preliminary steps are taken. An intravascular guidewire 100 can be inserted into a patient's vasculature, such as at a wrist (e.g., radial artery) or femoral vascular access point of the patient. The guidewire 100 can be fluoroscopically guided through the patient's vasculature to the patient's heart and into a coronary vessel presenting an ostial lesion to be stented, such as via the ostium of that coronary vessel, such as shown in FIG. 1A.

Figure 3:
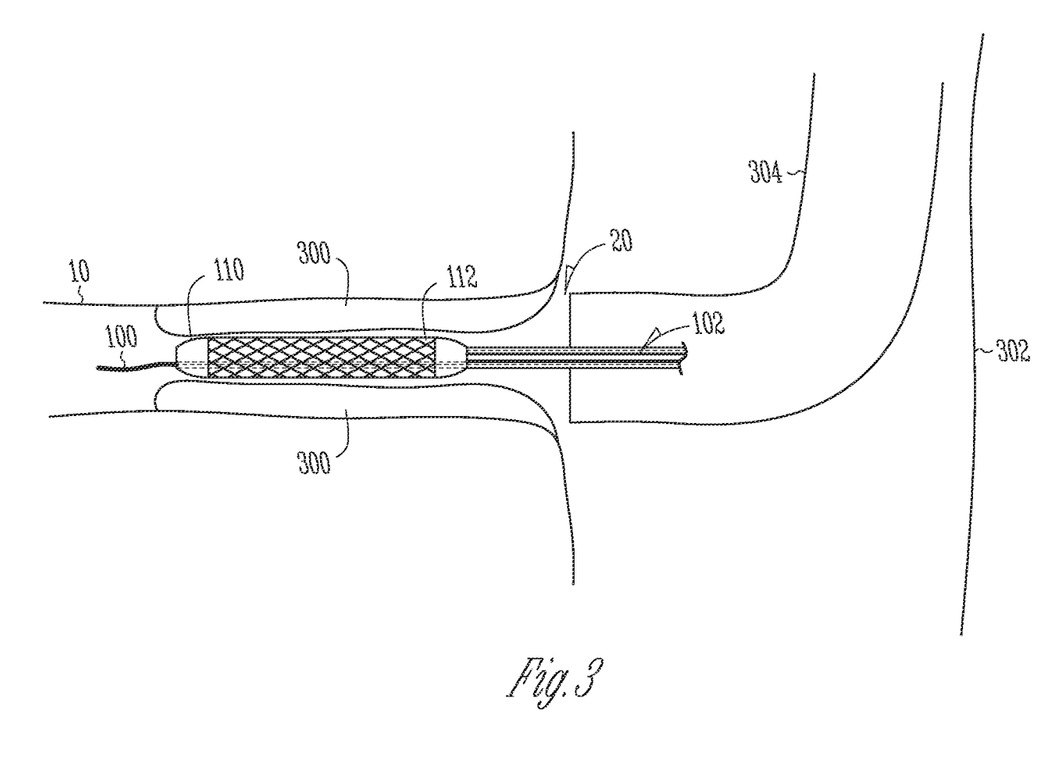
FIG. 3 shows a schematic illustration of the stent delivery device with the stent unexpanded at an ostial lesion, with the guide catheter routing the stent delivery device back through the vasculature.

More particularly, in a coronary ostium stenting example, first, access to the vasculature can be obtained at a radial or femoral artery access point. A 10 cm sheath can be introduced at the access point. The sheath can include one or more valved ports through which one or more other instruments can then be inserted. Next, an atraumatic J-tip wire (e.g., 0.035 inch diameter) can be introduced via the port in the sheath and advanced through the vasculature, such as up to the aortic valve, as can be observed fluoroscopically. Then, using a "co-pilot" two-port extension manifold inserted into the sheath, a JR4 guide catheter (e.g., with a 2 mm inner diameter lumen) can be inserted over the J-tip guidewire until its distal end reaches the mouth of the coronary artery 10. A distal end of the JR4 guide catheter can be manipulated into the mouth of the coronary artery 10, i.e., the coronary ostium 20, such as shown in FIG. 3. The J-tip wire can then be removed. A contrast-agent enhanced fluid can be introduced via the JR4 guide catheter and observed angiographically to confirm that the distal end of the JR4 guide catheter has been properly introduced into the coronary ostium 20. The thinner (0.014 inch) intravascular guidewire 100 can then be introduced into the coronary artery via the JR4 guide catheter.

At 202 of FIG. 2A, after this thinner guidewire 100 is in place, within the JR4 guide catheter, the stent delivery device 102, with its distal portion including its balloon 110 carrying a stent 112, can be inserted along the pathway of the guidewire 100. The guidewire 100 is threaded through a guidewire delivery lumen 118 of the stent delivery device 102, to introduce and pass the distal portion of the stent 102 delivery device 102 along the guidewire 100. This can include using either an over-the-wire (OTW) technique or a monorail/rapid exchange technique. The monorail/rapid exchange technique employs a shorter guidewire delivery lumen 118 or constraint than an OTW technique, as explained above. The introduction of the stent delivery device 102 can be observed fluoroscopically, if desired. However, as explained herein, neither fluoroscopy nor angiography will necessarily provide sufficiently detailed imaging information to allow the physician to determine proper placement of the stent 112, such as with a proximal end of the stent properly aligned with a plane defined by the ostium opening into the aorta.

At 204, after placing the distal portion of the stent delivery device 102 located within the vasculature such that the stent 112 is approximately at its desired placement and deployment location with respect to the ostial lesion to be stented, the ostium 20 can be imaged by the IVUS transducer 126 that is located onboard the distal portion of the stent delivery device 102. Such 360 degree circumferential imaging information from the BTUS imaging transducer 126 can be communicated to an external signal processor and displayed on a display screen. The displayed IVUS imaging information can help the user determine the location of the stent 112 with respect to the ostium. With such onboard IVUS imaging information available to the user at the time of stent placement, the user can slightly further insert or retract the stent delivery device 102 along the guidewire 100 until a proximal edge of the stent 112 is aligned with the plane defined by the ostial opening of the ostium 20.

With the imaging transducer 126 located onboard the stent delivery device 102 just proximal to the balloon 110 carrying the stent 112, good 360 degree circumferential information can be obtained for visualizing the plane defined by the ostial opening of the ostium 20, for visualizing a proximal edge of the stent 112, and for visualizing alignment between the two, as desired for proper ostial stent placement.

At 206, when the IVUS imaging indicates that the stent 112 is at this desired location with respect to the ostium 20 (e.g., proximal edge of the stent aligned with the plane defined by the ostial opening of the ostium 20) then the user can expand the balloon 110 to expand and deploy the stent 112 at the desired location with respect to the ostium 20. Using this approach, proper stent placement can be determined using onboard imaging, without having to withdraw the stent delivery device 102 to insert a separate IVUS probe along the guidewire 100 to perform imaging, followed by re-insertion of the stent delivery device 102 to use any imaging information provided by the separate IVUS probe.

In practice, at 204 and 206, the specified offset distance spacing between the proximal edge of the stent 112 and the IVUS transducer 126 can be used together with a pullback technique to place the stent 112 with its proximal edge aligned with the plane defined by the ostium 20 opening into the aorta. More particularly, the distal portion of the stent delivery device 102 can be inserted to position the stent 112 within the coronary blood vessel 10 with the IVUS transducer 126 located slightly distal to the plane defined by the ostium 20 opening into the aorta. Then, the pullback motor/actuator of the IVUS interface componentry 128 can provide mechanized pullback while the IVUS transducer 126 performs circumferential imaging. The IVUS images created during pullback can be stitched together to form a cylindrical image. When these image indicate that the IVUS transducer 126 is aligned with the plane defined by the ostium 20 opening into the aorta, the user can command the pullback motor/actuator of the IVUS interface componentry 128 to further pull back the stent delivery device 102 by an amount of the specified offset distance spacing between the proximal edge of the stent 112 and the IV US transducer. Doing so will position the proximal edge of the stent 112 aligned with the plane defined by the ostium 20 opening into the aorta.

Further, an even longer pullback can similarly be used pre-deployment to verify that the entire lesion will be supported by the stent 112. More particularly, it is desired that the stent 112 be placed such that it spans the ostial lesion to be treated, otherwise dissection of atherosclerotic tissue at the distal edge of the stent 112 can occur, which can reduce the efficacy of the stenting procedure and can lead to complications. By inserting the stent delivery apparatus 102 such that the IVUS transducer 126 is located more distal to a distal edge of the lesion, and creating a stitched-together cylindrical IVUS image by mechanized pullback from such initial insertion location until the IVUS transducer 126 is located in alignment with the plane defined by the ostium 20 opening into the aorta, the distance that will be spanned by the stent 112 to be deployed can be verified, pre-deployment, since the offset distance from the IVUS transducer 126 to each of the proximal and distal edges of the stent 112 is known. The IVUS images created during pre-deployment pullback can therefore include both images at or near a distal edge of the stent 112 and images at or near a proximal edge of the stent 112, such that proper placement of both edges of the stent 112 can be assessed, pre-deployment, without requiring removal of the stent delivery apparatus 102.

Figure 2B:
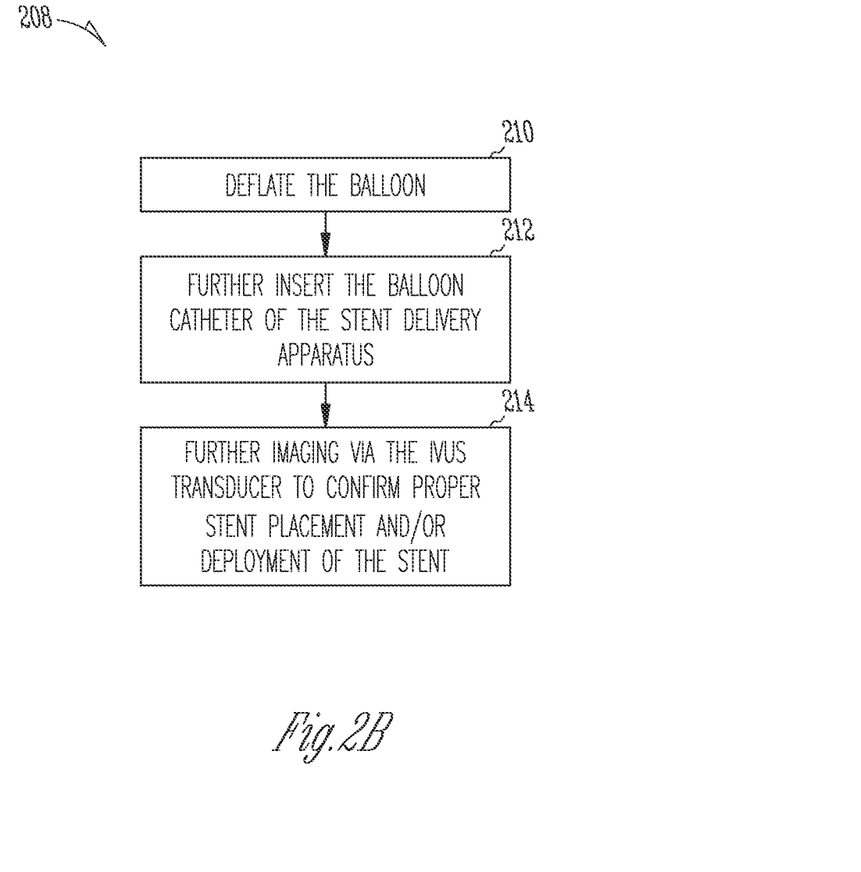
FIG. 2B is a flow chart showing an example of portions of a method of using onboard imaging of a stent delivery device to confirm proper placement of the stent, after expanding and deploying the stent at the desired location using the balloon of the balloon catheter provided by the stent delivery device.

FIG. 2B is a flow chart showing an example of portions of a method. 208 of using onboard imaging of a stent delivery device 102 to confirm proper placement of the stent 112, after expanding and deploying the stent 112 at the desired location using the balloon 110 of the balloon catheter provided by the stent delivery device 102.

At 210, after expanding the balloon 110 to expand and deploy the stent 112, the balloon 110 can be deflated.

At 212, after deflating the balloon 110, the stent delivery apparatus 102 can be slightly further advanced into the coronary vessel beyond its ostium 20. This will locate the onboard IVUS transducer 126 (which is just proximal to the balloon 110) into coaxial interior alignment with a proximal edge of the stent 112.

At 214, after such slightly further advancement of the distal portion of the stent delivery apparatus 102, further IVUS imaging using the onboard IVUS transducer 126 can be performed. Such imaging can confirm that the edge of the stent 112 is properly aligned with the plane of the ostial opening of the ostium 20, without the proximal edge of the stent 112 being located too deep within the coronary vessel to provide desired stenting of the ostial lesion at the ostium 20, and without the proximal edge of the stent 112 protruding out beyond the ostium 20 into the vasculature.

In practice, at 212 and 214, it may be desired, after deflating the balloon 110, to advance the stent delivery apparatus 102 further into the coronary vessel such that the IVUS transducer 126 is located even more distal than a distal edge of the stent 112, and the mechanized pullback provided by the IVUS interface componentry 128 can be used to create stitched-together cylindrical image of the coronary vessel distal to the stent 112, including at the distal boundary of the stent 112. It is desired that the stent 112 be placed such that it spans the ostial lesion to be treated, otherwise dissection of atherosclerotic tissue at the distal edge of the stent 112 can occur, which can reduce the efficacy of the stenting procedure and can lead to complications. In sum, confirmation of proper placement of the stent 112 can include using the IVUS imaging not only to verify proper placement of the proximal edge of the stent 112, but also, to verify proper placement of the distal edge of the stent 112. The IVUS images created during pullback can therefore include both images at or near a distal edge of the stent 112 and images at or near a proximal edge of the stent 112, which can be obtained during the same or different pullbacks, and which need not require removal of the stent delivery apparatus to perform such imaging confirmation.

In FIGS. 2A, 2B, the onboard IVUS imaging for pre-placement stent location determination and for post-placement stent placement and deployment confirmation can each be performed (1) using an onboard. IVUS transducer 112 that is fixed with respect to the balloon 110; or (2) using an onboard IVUS transducer 112 that is on a removable probe that can be inserted via the IVUS hypotube 106 into a desired position with respect to the balloon 110 and then removed via the IVUS hypotube 106—without requiring removal of the stent delivery device 102 from the guidewire 110 because of the IVUS hypotube 106 is fixed to the balloon inflation hypotube 104 along the shared elongate shaft 108. In this way, the IVUS hypotube 106 can provide an IVUS lumen, such as the IVUS lumen 116, with allows a fixed IVUS transducer 126 to be connected via a signal communication conduit, such as an electrical or optical signal conductor, to external signal processing componentry. Similarly, the IVUS hypotube 106 can provide an IVUS lumen, such as the IVUS lumen 116, which allows a removable IVUS transducer 126 located on a probe inserted into the IVUS lumen 116 to be retracted therefrom after imaging, such as for re-sterilization and re-use in a subsequent procedure, if desired.

Figure 2C:
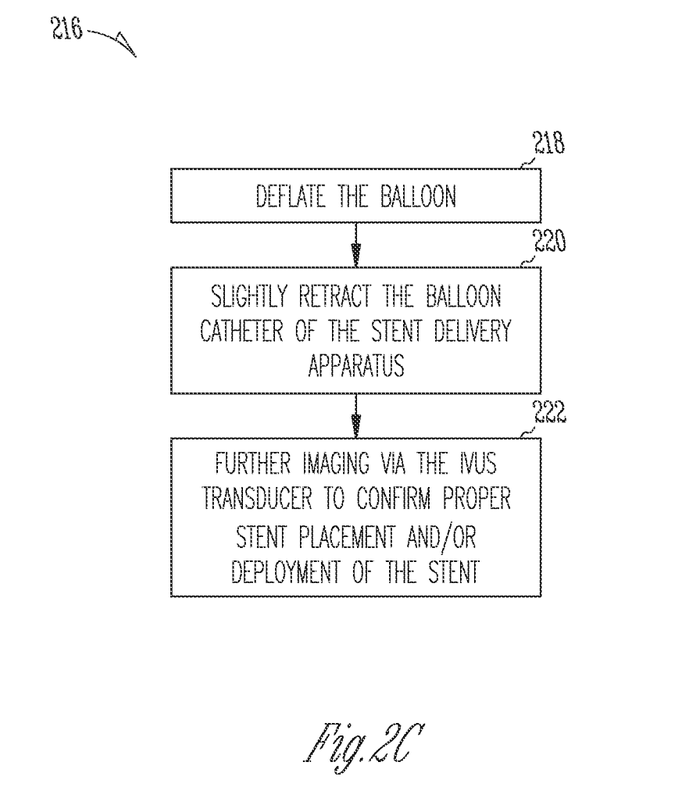
FIG. 2C is a flow chart illustrating portions of a method, similar to the method in FIG. 2B, but in which instead of further inserting the balloon catheter of the stent delivery apparatus, after deflating the balloon, in FIG. 2C, the balloon catheter of the stent delivery apparatus is slightly retracted for performing the IVUS imaging for confirming stent placement.

FIG. 2C is a flow chart illustrating portions of a method 216, similar to the method 208 in FIG. 2B, but in which instead of further inserting the balloon catheter of the stent delivery apparatus 102 at 212, after deflating the balloon at 210, in FIG. 2C, at 220, the balloon catheter of the stent delivery, apparatus 102 is slightly retracted for performing the IVUS imaging for confirming stent placement. This may be useful, for example, if the stent was introduced and placed too far into the coronary blood vessel, such that a slight retraction of the stent delivery apparatus 102 is helpful to align the 360 degree circumferential imaging of the IVUS transducer 126 with the plane of the ostial opening of the ostium 20 to view and analyze stent placement and/or deployment.

FIG. 3 shows a schematic illustration of the stent delivery device 102 with the balloon 110 carrying the unexpanded stent 112 at an ostial lesion 300, with the guide catheter 304 routing the stent delivery device 102 back through the vasculature of the aorta 302.

Figure 4:
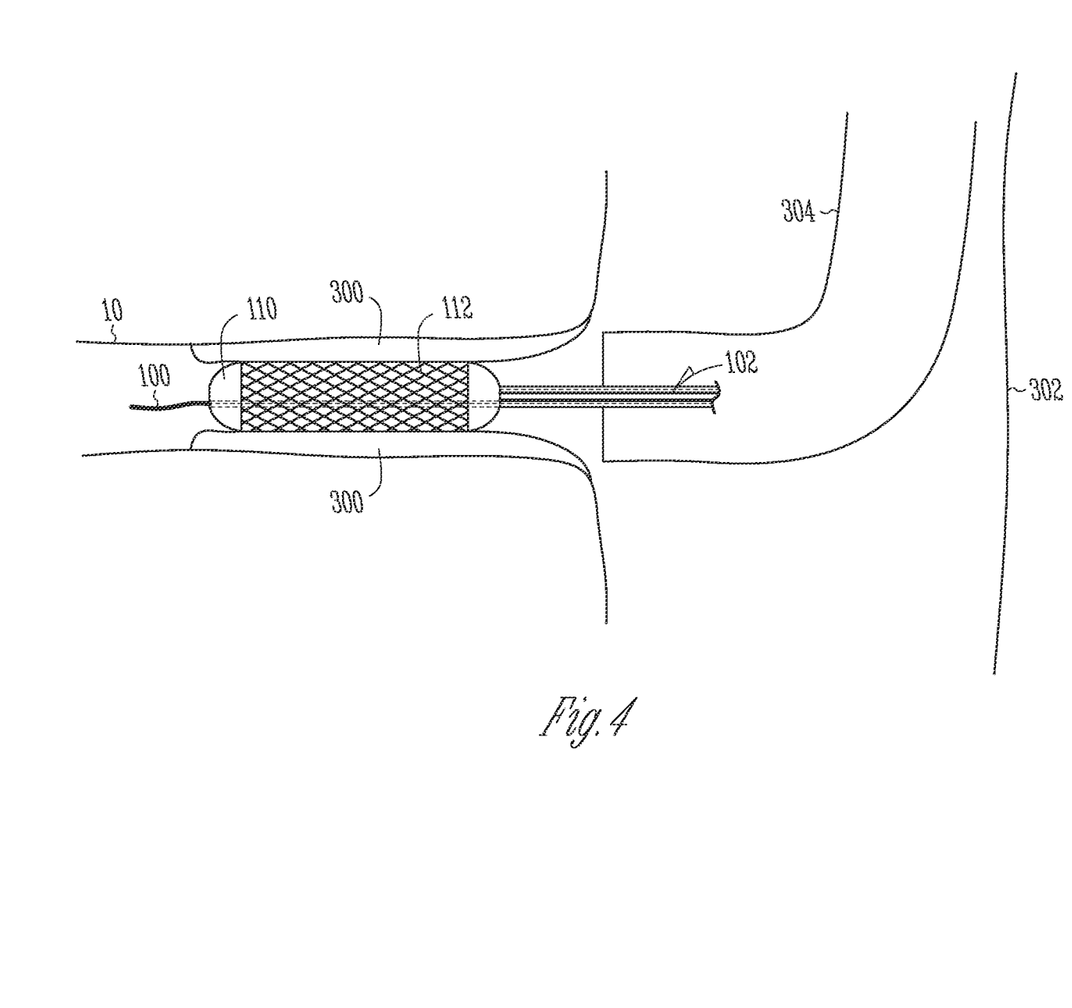
FIG. 4 is similar to FIG. 3, but with the stent having been expanded by the balloon.

FIG. 4 is similar to FIG. 3, but with the stent 112 having been expanded by the balloon 110.

The above description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round," a component that is not precisely circular (e.g., one that is slightly oblong or is a many-sided polygon) is still encompassed by this description.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, s the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The invention claimed is:

1. An integrated intravascular ultrasound (IVUS) ostial stent delivery apparatus, the apparatus comprising:
    a balloon catheter, including:
    a unitary elongate shaft having a proximal shaft portion and a distal shaft portion;
    a balloon located at and circumferentially about the distal shaft portion;
    wherein the shaft defines (1) a longitudinal inflation lumen in fluid communication with the balloon and (2) a longitudinal IVUS lumen extending between the proximal shaft portion and up to the balloon on the distal shaft portion, the IVUS lumen sized and shaped to accommodate a slidable IVUS ultrasound imaging transducer insertable into and slidable through the IVUS lumen; and (3) a longitudinal guidewire lumen, extending at least through the distal shaft portion underlaying the balloon for at least a length of the balloon along the shaft, wherein the inflation lumen, the IVUS lumen, and the guidewire lumen respectively define lumens that are separate and laterally offset from each other to permit independent operation of the inflation lumen, the IVUS lumen, and the guidewire lumen, and wherein the shaft comprises a first hypotube and a second hypotube non-concentrically attached laterally adjacent to each other to form a unitary elongate member providing the shaft, the second hypotube arranged adjacent to and laterally offset from the first hypotube along a length of the shaft extending from the proximal portion of the shaft to the balloon located at the distal portion of the shaft, and wherein the first hypotube defines the longitudinal inflation lumen and the second hypotube defines the IVUS lumen through which the transduced IVUS signal conduit is passed;
    the transducer, user-slidable with respect to the balloon within the IVUS lumen via a user-insertable and user-removable elongate IVUS catheter member sized and shaped to be slidably passed through the IVUS lumen to permit user-adjustment of a location of the transducer with respect to the balloon to permit imaging of a blood vessel ostium including before expandably deploying a stent at or near the ostium by inflating the balloon; and
    a transduced IVUS signal conduit, coupled to the transducer and passing through the IVUS lumen to the proximal shaft portion for coupling to a patient-external IVUS interface for signal processing by patient-external processing circuitry couplable to the IVUS signal conduit; and
    wherein the transducer and the IVUS signal conduit are attached to each other as part of the user-insertable and user-removable elongate IVUS catheter member sized and shaped to be slidably passed through the IVUS lumen by user-manipulation of the elongate IVUS catheter member from a location proximal to a proximal end of the shaft to permit the user to adjustably position the transducer with respect to the balloon.

2. The apparatus of claim 1, wherein the transducer is affixed within the second hypotube at the distal portion of the shaft.

3. The apparatus of claim 1, wherein the transducer is located adjacent a portion of the second hypotube that is made of a non-metallic ultrasound transmissive material.

4. The apparatus of claim 1, wherein the first hypotube extends along at least a portion of the shaft adjacent to the second hypotube.

5. The apparatus of claim 1, wherein the second hypotube comprises a non-metallic material so as to be capable of transmitting ultrasound therethrough.

6. The apparatus of claim 1, wherein the first hypotube comprises a nonmetallic material at the distal portion of the shaft and a metallic material at the proximal portion of the shaft.

7. The apparatus of claim 1, wherein the transducer is affixed within the distal shaft portion of the shaft.

8. The apparatus of claim 1, wherein the IVUS catheter member is made of one or more materials that are sterilization-compatible to allow for sterilization and re-use of the IVUS catheter member.

9. A method of deploying a stent at a blood vessel ostium, the method comprising:
    inserting, using a guidewire carried by a guidewire lumen, both an IVUS ultrasound imaging transducer and a balloon carrying a stent into the ostium, both the transducer and the balloon carried by a balloon catheter of a stent delivery apparatus, wherein the transducer is slidably adjustably user-positionable, with respect to the balloon, within a transducer lumen of the balloon catheter;

imaging the ostium from a transducer at a user-adjustable position of the transducer with respect to the balloon, the user-adjustable position located within the balloon catheter of the stent delivery apparatus including within the transducer lumen at a location proximally to the balloon carrying the stent to determine a stent location; and using the imaging, positioning the stent at a desired stent location with a proximal edge of the stent aligned to the ostium, then expanding the balloon using an inflation lumen to expandably deploy the stent with a proximal edge of the stent aligned to the ostium so as to avoid protruding out from the ostium into the blood vessel, wherein the inflation lumen, the IVUS lumen, and the guidewire lumen respectively define lumens that are separate and laterally offset from each other on a shaft to permit independent operation of the inflation lumen, the IVUS lumen, and the guidewire lumen, and wherein the shaft comprises a first hypotube and a second hypotube non-concentrically, attached laterally adjacent to each other to form a unitary elongate member providing the shaft, the second hypotube arranged adjacent to and laterally offset from the first hypotube along a length of the shaft extending from the proximal portion of the shaft to the balloon located at the distal portion of the shaft, and wherein the first hypotube defines the longitudinal inflation lumen and the second hypotube defines the IVUS lumen through which a transduced IVUS signal conduit is passed.

10. The method of claim 9, further comprising:
deflating the balloon;
further inserting or retracting the balloon catheter of the stent delivery apparatus; and
further imaging via the transducer to confirm stent deployment.

11. The method of claim 9, wherein inserting both the transducer and the balloon comprises inserting the transducer within the balloon catheter providing the balloon, wherein the transducer is in a fixed arrangement with respect to the balloon.

12. The method of claim 9, wherein inserting both the transducer and the balloon comprises user-inserting the transducer to a desired location with respect to the balloon via an IVUS lumen within an elongate shaft of the balloon catheter providing the balloon.

13. The method of claim 12, further comprising removing the ultrasound transducer by extracting the transducer via the IVUS lumen to an external location.

14. The od of claim 13, comprising reprocessing the ultrasound transducer, including resterilization, for reusing the ultrasound transducer for a subsequent procedure.

15. The method of claim 9, wherein the inserting the balloon includes inserting a portion of the balloon catheter using a monorail/rapid-exchange technique.

16. The method of claim 9, wherein inserting the balloon includes inserting a portion of the balloon catheter using an over-the-wire technique.

17. The method of claim 9, wherein:
imaging the ostium is included together with imaging the blood vessel during a pullback of the transducer; and aligning the transducer with the ostium, then retracting the stent delivery apparatus by a specified amount to align a proximal edge of the stent with the ostium.

18. The method of claim 9, comprising imaging the blood vessel at a distance from the ostium corresponding to a distal edge of the stela when the proximal edge of the stent is aligned with the ostium.

19. The method of claim 18, wherein the imaging the ostium and the imaging the blood vessel at a distance from the ostium corresponding to a distal edge of the stent when the proximal edge of the stent is aligned with the ostium, are both performed during a single pullback of the transducer.

20. An integrated intravascular ultrasound (IVUS) ostial stent delivery apparatus, the apparatus comprising:
a unitary elongate shaft having a proximal shaft portion and a distal shaft portion, the shaft defining both (1) a longitudinal inflation lumen and (2) a separate and laterally offset longitudinal IVUS lumen extending between the proximal shaft portion and the distal shaft portion;
a balloon located at and circumferentially about the distal shaft portion and in fluid communication with the inflation lumen, and
wherein the shaft further defines a longitudinal guidewire lumen, separate and laterally offset from the inflation lumen and the IVUS lumen, the guidewire lumen extending at least through the distal shaft portion underlaying the balloon for at least a length of the balloon along the shaft, wherein the inflation lumen, the IVUS lumen, and the guidewire lumen respectively define lumens that are separate and laterally offset from each other to permit independent operation of the inflation lumen, the IVUS lumen, and the guidewire lumen, and wherein the shaft comprises a first hypotube and a second hypotube non-concentrically attached laterally adjacent to each other to form a unitary elongate member providing the shaft, the second hypotube arranged adjacent to and laterally offset from the first hypotube along a length of the shaft extending from the proximal portion of the shaft to the balloon located at the distal portion of the shaft, and wherein the first hypotube defines the longitudinal inflation lumen and the second hypotube defines the IVUS lumen through which the transduced IVUS signal conduit is passed;
wherein the IVUS lumen is sized and shaped and arranged to receive an IVUS ultrasound imaging transducer slidable therethrough, to permit a user, after deployment of the distal shaft portion of the unitary elongate shaft, to slidably pass through the IVUS lumen a user-insertable and user-removable elongate IVUS catheter member, including the transducer and an IVUS signal conduit, to a location that is adjustable by the user with respect to the balloon at or just proximal to the balloon to permit user-positioning of the transducer with respect to the balloon for imaging of a blood vessel ostium including before expandably deploying a stent at the ostium by inflating the balloon.

21. The apparatus of claim 20, further comprising:
the IVUS ultrasound imaging transducer; and
a transduced IVUS signal conduit coupled to the transducer and passing through the IVUS lumen to the proximal shaft portion for coupling to a patient-external IVUS interface for signal processing by patient-external processing circuitry couplable to the IVUS signal conduit.

22. The apparatus of claim 20, wherein the shaft comprises a first hypotube and a second hypotube attached to each other to form a unitary elongate member providing the shaft, the second hypotube arranged adjacent to the first hypotube along a length of the shaft extending from the proximal portion of the shaft to the balloon located at and about the distal portion of the shaft.

23. The apparatus of claim 22, wherein the first and second hypotubes are arranged together longitudinally to be adjacent and affixed to each other.

* * * * *

UNITED STATES PATENT AND TRADEMARK OFFICE
CERTIFICATE OF CORRECTION

| | | |
|---|---|---|
| PATENT NO. | : 11,510,798 B1 | Page 1 of 1 |
| APPLICATION NO. | : 17/472450 | |
| DATED | : November 29, 2022 | |
| INVENTOR(S) | : Arunpreet Kahlon | |

It is certified that error appears in the above-identified patent and that said Letters Patent is hereby corrected as shown below:

In the Claims

In Column 15, Line 26, in Claim 9, delete "non-concentrically," and insert --non-concentrically-- therefor In Column 15, Line 56, in Claim 14, delete "od" and insert --method-- therefor In Column 16, Line 6, in Claim 18, delete "stela" and insert --stent-- therefor Signed and Sealed this
Twenty-sixth Day of September, 2023

*Katherine Kelly Vidal*

Katherine Kelly Vidal
*Director of the United States Patent and Trademark Office*